United States Patent
Hajij et al.

(10) Patent No.: US 12,051,512 B2
(45) Date of Patent: Jul. 30, 2024

(54) MULTIMODAL CELL COMPLEX NEURAL NETWORKS FOR PREDICTION OF MULTIPLE DRUG SIDE EFFECTS SEVERITY AND FREQUENCY

(71) Applicants: Santa Clara University, Santa Clara, CA (US); University of South Florida, Tampa, FL (US); The Regents of the University of California, Oakland, CA (US)

(72) Inventors: Mustafa Hajij, Santa Clara, CA (US); Ghada Alzamzmi, Rockville, MD (US); Nina Miolane, Santa Barbara, CA (US)

(73) Assignees: Santa Clara University, Santa Clara, CA (US); The Regents of the University of California, Oakland, CA (US); University of South Florida, Tampa, FL (US)

( * ) Notice: Subject to any disclaimer, the term of this patent is extended or adjusted under 35 U.S.C. 154(b) by 169 days.

(21) Appl. No.: 17/950,906

(22) Filed: Sep. 22, 2022

(65) Prior Publication Data
US 2023/0086217 A1 Mar. 23, 2023

Related U.S. Application Data

(60) Provisional application No. 63/247,008, filed on Sep. 22, 2021.

(51) Int. Cl.
*G16H 70/40* (2018.01)
*G06N 7/01* (2023.01)
*G16H 10/60* (2018.01)

(52) U.S. Cl.
CPC ............ *G16H 70/40* (2018.01); *G06N 7/01* (2023.01); *G16H 10/60* (2018.01)

(58) Field of Classification Search
None
See application file for complete search history.

(56) References Cited

U.S. PATENT DOCUMENTS

2020/0342954 A1* 10/2020 Ui .................... G16B 40/00

OTHER PUBLICATIONS

TEX. Why do the less than symbol (<) and the greater than symbol (>) appear wrong as upside down exclamation (¡) or question mark (¿)? Stack Exchange. 2010. <URL: https://tex.stackexchange.com/questions/2369/why-do-the-less-than-symbol-and-the-greater-than-symbol-appear-wrong-as> (Year: 2010).*

(Continued)

*Primary Examiner* — Bion A Shelden
(74) *Attorney, Agent, or Firm* — LUMEN PATENT FIRM

(57) ABSTRACT

A method for predicting side effects of a combination of drugs administered concurrently includes training a multimodal cell complex neural network (MCXN) on a dataset. The MCXN includes nodes representing the drugs and proteins, pair-wise relationships between nodes representing interactions between pairs of drugs and/or proteins, and k-wise relationships between the nodes representing interactions between k drugs and/or proteins, where k¿2. The training dataset includes a list of drugs, a list of proteins, and pharmacological information about the drugs in the list of drugs and proteins in the list of proteins. A specification of the combination of at least three drugs to be administered concurrently is input to the MCXN which predicts probabilities that administering the combination of drugs concurrently results in potential side effects. It also predicts both frequencies of the potential side effects and severities of the potential side effects.

7 Claims, 4 Drawing Sheets

(56) References Cited

OTHER PUBLICATIONS

M Hajij et al. Cell Complex Neural Networks. arXiv. Oct. 2, 2020. <URL:https://arxiv.org/abs/2010.00743v1> (Year: 2020).*

M Zitnik et al. Modeling polypharmacy side effects with graph convolutional networks. arXiv. Apr. 26, 2018. <URL:https://arxiv.org/pdf/1802.00543 (Year: 2018).*

X Hou et al. Predicting Drug-Drug Interactions Using Deep Neural Network. ICMLC '19. Feb. 22, 2019. <URL:https://dl.acm.org/doi/10.1145/3318299.3318323> (Year: 2019).*

Y Deng et al. A multimodal deep learning framework for predicting drug-drug interaction events. Bioinformatics. May 14, 2020. <URL:https://academic.oup.com/bioinformatics/article/36/15/4316/5837109> (Year: 2020).*

K Han. A Review of Approaches for Predicting Drug-Drug Interactions Based on Machine Learning. Front Pharmacol. Jan. 28, 2022. <URL:https://www.ncbi.nlm.nih.gov/pmc/articles/PMC8835726/> (Year: 2022).*

YH Feng et al. DPDDI: a deep predictor for drug-drug interactions. BMC Bioinformatics. Sep. 24, 2020. <URL:https://bmcbioinformatics.biomedcentral.com/articles/10.1186/s 12859-020-03724-x> (Year: 2020).*

Hajij et al., Cell Complex Neural Networks, NeurIPS 2020 Workshop TDA and Beyond Program, Oct. 30, 2020.

Hajij et al., Cell Complex Neural Networks, Mar. 2, 2021, arXiv:2010.00743v4 [cs.LG].

Zitnik, et al., Modeling polypharmacy side effects with graph convolutional networks, May 18, 2018. bioRxiv preprint doi: 10.1101/258814.

Kwak, et al., Drug-disease graph: Predicting adverse drug reaction signals via graph neural network with clinical data, arXiv:2004.00407v1 [cs.LG] Apr. 1, 2020.

Timilsina, et al., Discovering links between side effects and drugs using a diffusion based method, Scientific reports 9 (2019), No. 1, 1-10.

Zhang, et al., A unified frame of predicting side effects of drugs by using linear neighborhood similarity, BMC systems biology 11 (2017), No. 6, 23-34.

Galeano, et al., Predicting the frequencies of drug side effects, Nature communications 11 (2020), No. 1, 1-14.

Zhao, et al., A similarity-based method for prediction of drug side effects with heterogeneous information, Mathematical biosciences 306 (2018), 136-144.

Wang, et al., Exploring the associations between drug side-effects and therapeutic indications, Journal of biomedical informatics 51 (2014), 15-23.

Wang, et al., Deepdds: deep graph neural network with attention mechanism to predict synergistic drug combinations, bioRxiv (Jul. 6, 2021). doi: 10.1101/2021.04.06.438723.

* cited by examiner

MULTIMODAL CELL COMPLEX NEURAL NETWORKS FOR PREDICTION OF MULTIPLE DRUG SIDE EFFECTS SEVERITY AND FREQUENCY

CROSS-REFERENCE TO RELATED APPLICATIONS

This application claims priority from U.S. Provisional Patent Application 63/247,008 filed Sep. 22, 2021, which is incorporated herein by reference.

FIELD OF THE INVENTION

The present invention related generally to prediction of side-effects when multiple drugs are administered in combination. More specifically, it relates to techniques for predicting drug side-effects using neural networks.

BACKGROUND OF THE INVENTION

Predicting the unintended side effects of a new drug is a critical issue in pharmacological studies. Drug side effects can be defined as unexpected body's responses beyond the drugs' anticipated therapeutic effects. Such responses can significantly impact human's health, degrade the quality of their lives, cause emotional distress, and even death. In fact, severe drug reactions are one of the leading causes of morbidity and mortality in healthcare globally, and it is the fourth cause of death in the United States. Further, severe side effects can cause significant economic burden and clinical costs as they often lead to prolonged hospitalization and frequent emergency visits. In the United States, the financial burden of adverse side effects was estimated to be as high as 30.1 billion dollars annually.

Drugs can be broadly divided into monotherapy or polytherapy, where monotherapy refers to the use of a single drug to treat a disease/condition while polytherapy refers to the use of multiple drugs. As compared to polytherapy, monotherapy has several advantages including better tolerability and compliance, avoidance of drug-drug interactions, and reduced treatment costs. However, the use of multiple drugs might be inevitable for treating patients with complex conditions, co-existing conditions, multiple diseases or multimorbidity. Further, the use of polypharmacy may in some cases improve treatment efficacy, prevent the development of drug resistance, and reduce the duration of treatment. While polytherapy has been widely practiced for treating many diseases, it has been increasing the risk of severe side effects occurring as a result of drug-drug interactions. Due to this issue, polypharmacy's side effects is still a major problem in healthcare affecting approximately 15% of the United States population and costing more than $177 billion annually.

The traditional methods for determining the side effects of drugs face the problems of long development time as well as high resources and cost. For example, intensive monitoring in hospitals is a common way to discover adverse drug reactions by recording all adverse events of the drug in a specific area and period. Although this method can be accurate and reliable, it takes a lot of time (months to years) and expense due to the need for long-term testing of all drug users in the testing area. Further, the manual identification of polypharmacy side effects is impracticable as it is practically infeasible to capture all possible pairs of drug-drug interactions. Another method involves using a daily medication log or diary to track medication's dosages and side effects. Although this method (patients' self reports) represents the gold standard used by doctors to monitor patient's side effects, it is time-consuming, inconsistent, and inefficient. Therefore, computational methods, which we review below, for the accurate prediction of substitute drugs and side effects have become an ideal transform for achieving safe medication use.

Recently, there has been an increasing interest to discover drug-drug interactions and identify drugs' side effects using computational methods. In this section, we present a literature review of current computational methods as well as a summary of our contributions.

Existing approaches to predict the presence or severity of a specific drug or combinations of drugs may be classified based on the underlying algorithm used: graph-based methods and matrix-based similarity methods.

Graph Neural Networks (GNNs) are a class of deep learning methods designed to perform inference on data described by graphs. Generally speaking, graphs are used to describe and analyze entities with relationships or interactions. In the case polypharmacy problem, these entities represent different drugs or proteins, and the edges represent the interactions between different drugs, different proteins, or drugs and proteins. Existing techniques have used GNNs to analyze drugs' relationships and predict the severity of their side effects. For example, Zitnik et al. (Modeling polypharmacy side effects with graph convolutional networks, Bioinformatics 34 (2018), no. 13) proposed Decagon, an approach for modeling polypharmacy side effects. The approach constructed a multimodal graph of protein-protein interactions, drug-protein interactions, and the polypharmacy side effects, which are represented as drug-drug interactions. Decagon achieved excellent performance in predicting polypharmacy side effects and outperformed the baselines (traditional approach) by up to 69%. Similarly, Kwak et al. (Drug-disease graph: Predicting adverse drug reaction signals via graph neural network with clinical data, Advances in Knowledge Discovery and Data Mining 12085 (2020), 633) presented a GNN-based method to predict severe side effects labels from the Side Effect Resource (SERD) database (The sider database of drugs and side effects, Nucleic acids research 44 (2016), no. D1, D1075-D1079).

Although GNN-based methods achieved excellent performance in predicting drugs' side effects and their severity, there are multiple main drawbacks of utilizing graph neural networks for this prediction problem. The most important drawback is that graphs can only model pairwise relationships. Specifically, a graph can only model side effects between two drugs and hence these models cannot model more than two drugs that interact when taken concurrently. This is clearly rather restrictive because a patient might have to take more than two drugs concurrently.

Finally, from a computational perspective, graph neural network message passing schemes have been shown recently to have limited expressive power capabilities. The expressive power of a graph neural network is a theoretical measure for its capacity to perform accurate prediction across different tasks in practice. In general, networks with less expressive power perform less accurately on prediction tasks. The expressive power of a given network is usually measured by the Weisfeiler Lehman (WL) graph isomorphism test and its hierarchical version, the k-WL test. These tests form a sequence of increasingly more discriminative tests such that the (k+1)-WL test strictly provides a more discriminative and powerful test than the k-WL tests for all $k \geq 1$. In other words, theoretically higher order tests are able to distinguish between larger set graphs. In practice, this higher expressiveness is associated with more accurate and robust predictions. Graph neural networks message passing schemes have been proven to be as powerful as the WL test. Most existing graph neural networks do not pass the 1-WL test. Recently, Xu et al. (How powerful are graph neural networks?, arXiv preprint arXiv:1810.00826 (2018)) proposed an architecture that can be as expressive as the k-WL test for any k. However, their work suffers from very high computational and memory complexity, making it impractical to implement in practice.

Matrix-based similarity is another type of method that has been used for predicting the severity of drugs' side effects. Using matrix-based similarity methods, the pairwise similarities between drugs are measured, where greater similarity between two drugs generates greater value of the measure, and vice versa. Zhang et al. (A unified frame of predicting side effects of drugs by using linear neighborhood similarity, BMC systems biology 11 (2017), no. 6, 23-34) presented a method to calculate the linear neighborhood similarity in a drug feature space by exploring the linear neighborhood relationship followed by transferring the similarity from the feature space into the side-effect space. Finally, the drug side effects were predicted by propagating known side-effect information through a similarity-based graph.

Although several works show the feasibility of using similarity-based methods for side effects prediction, matrix-based methods have many limitations. First, matrix-based methods require manual labor and an extensive domain expertise for feature engineering and function engineering to achieve good results. From a technical perspective, matrix-based methods do not usually generalize well beyond intermediate-size scale datasets. Finally, similar to GNNs, matrix-based methods only model pairwise drug-drug interactions which (as discussed above) is often not realistic for practical scenarios. Contrary to graph-based and matrix-based methods, the present technology (MCXN) can model higher order drug-drug interactions in addition to pairwise interaction.

In addition to side effect severity, few works proposed to predict the frequency of a side-effect by classifying side effects into very frequent, frequent, very rare, and rare. The accurate prediction of the frequencies of side effects is important due to two main reasons. First, it is vital to patient care in clinical practice as it helps doctors making decisions. Second, the prediction of side-effect frequency is essential for pharmaceutical companies as it reduces the risk of drug withdrawal from the market as well as the costly reassessment of side-effect frequencies through new clinical trials.

Galeano et al. (Predicting the frequencies of drug side effects, Nature communications 11 (2020), no. 1, 1-14) presented a machine learning approach, based on a matrix decomposition algorithm, for predicting the frequencies of drug side effects. The proposed approach achieved area under the receiver operating characteristic values that range from 0.914±0.003 to 0.594±0.0084, when evaluated on 759 drugs and 994 side effects from all human physiological systems. Although the method achieved good prediction performance, it is difficult to integrate more useful features such as the similarity between drugs, structural information of drugs as well as the similarity between side effects in the learning process. Therefore, the generalization ability of the model is limited to a certain extent.

Another method for predicting the frequency of drugs' side effects is presented in Zhao et al. (A novel graph attention model for predicting frequencies of drug-side effects from multi-view data, Briefings in Bioinformatics (2021)). The proposed method used a multi-view graph convolutional model to integrate three different types of features, including similarity, association distribution, and word embedding. The experimental results demonstrated high effectiveness in 10-fold cross-validation, and showed that the proposed method outperformed the matrix decomposition model proposed in Galeano et al.

Existing methods were developed for either side effects severity prediction or side effects frequency prediction. However, drugs' side effects have two dimensions, and they vary in their severity and frequency of occurrence. Hence, understanding the status of a given drug (monotherapy) or drug combinations (polytherapy) on both these dimensions is important for physicians during the prescribing process, for regulators and industry in the approval and safety review process, and for patients in the compliance process.

As general changes in the patient's health status (physical or mental) often leads health professionals to prescribe new drugs, the addition of a new drug create a new drug combinations and might alter the side effects (in terms of severity or frequency) of previous drugs taken by the patient. Further, lifestyle (e.g., diet, smoking and alcohol habits) has an impact on drugs' side effects. Specifically, specific foods might impact how human's body absorbs, metabolizes, or responds to specific drugs. In addition, factors such as age, presence of other diseases, can change human body's reactions to drugs. We can conclude that drugs' side effects are dynamic and adaptable. Treating drugs' side effects prediction as a dynamic problem enables health professionals to adjust treatment plans based on observed changes in the side effects, and provides a new perspective in dealing with the decision making process of drug selection.

All existing works in the literature treat the problem of drugs' side effects prediction as static. We are not aware of any current work or computational tool that monitors and detects changes in side effects triggered by factors such as changes in the patient's health status or lifestyle.

BRIEF SUMMARY OF THE INVENTION

We use a recently developed technology, called multimodal cell complex neural networks (MCXNs), for predicting the severity and frequency of drugs' side effects. Specifically, the present technology uncovers the relationship among a k-combination of drugs taken concurrently and measures the probability that these combinations would have a certain side-effect or combination of side-effects r. The predicted side effect (frequency and severity) is then used to rank drugs or drug combinations from best to worst. We want to emphasize that current technologies (e.g., graph-based methods) can only model binary relations among data, thus not being applicable in the presence of multi-way or higher-order relations (higher-order drugs/protein interactions).

The present technology can also be used to measure how side effects change (in terms of frequency and severity) during the course of treatment. Such technology provides several benefits for patients, health professionals, and pharmaceutical companies. For example, predicting side effects of "candidates" drugs during the early stage of drug design and development can improve drug safety, speed up the development of new therapeutics, reduce patients' risks, and save money for the pharmaceutical companies. Further, personalized ranking of drugs or drug combinations (best to worse) while recommending better drug alternatives can significantly help health professionals developing a personalized treatment plan for each patient, and adjust this plan based on changes of the patient's health record/condition. Also, the present technology provides an efficient and accurate approach for managing patients' drugs and monitoring their impacts on patients.

In one aspect, the invention provides a method for predicting side effects of a combination of drugs administered concurrently, the method includes training a multi-modal cell complex neural network (MCXN) on a dataset, wherein the MCXN includes nodes representing the drugs and proteins, pair-wise relationships between nodes representing interactions between pairs of drugs and/or proteins, and k-wise relationships between the nodes representing interactions between k drugs and/or proteins, where k 2, wherein the dataset includes a list of drugs, a list of proteins, and pharmacological information about the drugs in the list of drugs and proteins in the list of proteins; wherein the pharmacological information about the drugs and the proteins include: i) physical binding information of the proteins, ii) interactions between the drugs and the proteins, iii) interactions between two or more of the drugs, including severity and frequency of side effects of the interactions. The method also includes inputting to the MCXN a specification of the combination of drugs to be administered concurrently, where the combination includes at least three drugs, wherein the at least three drugs includes a drug not included in the training set; and predicting from the MCXN probabilities that administering the combination of drugs concurrently results in potential side effects, and predicting both frequencies of the potential side effects and severities of the potential side effects.

The method may also include outputting a list of the probabilities of the potential side effects resulting from administering the combination of drugs concurrently, outputting a severity category of the potential side effects resulting from administering the combination of drugs concurrently, outputting a frequency category of the potential side effects resulting from administering the combination of drugs concurrently, and/or outputting ranked sublists of the input drugs ranked based on a combination of frequency and the severity of side effects.

In some embodiments, the method includes inputting to the MCXN prior patient health information over a time period and outputting resulting changes in frequency and severity of side effects over the time period. The prior patient health information over a time period may include changes in an administered drug, changes in a drug dose, changes in a health condition, or changes in lifestyle.

DETAILED DESCRIPTION OF THE INVENTION

Figure 1:
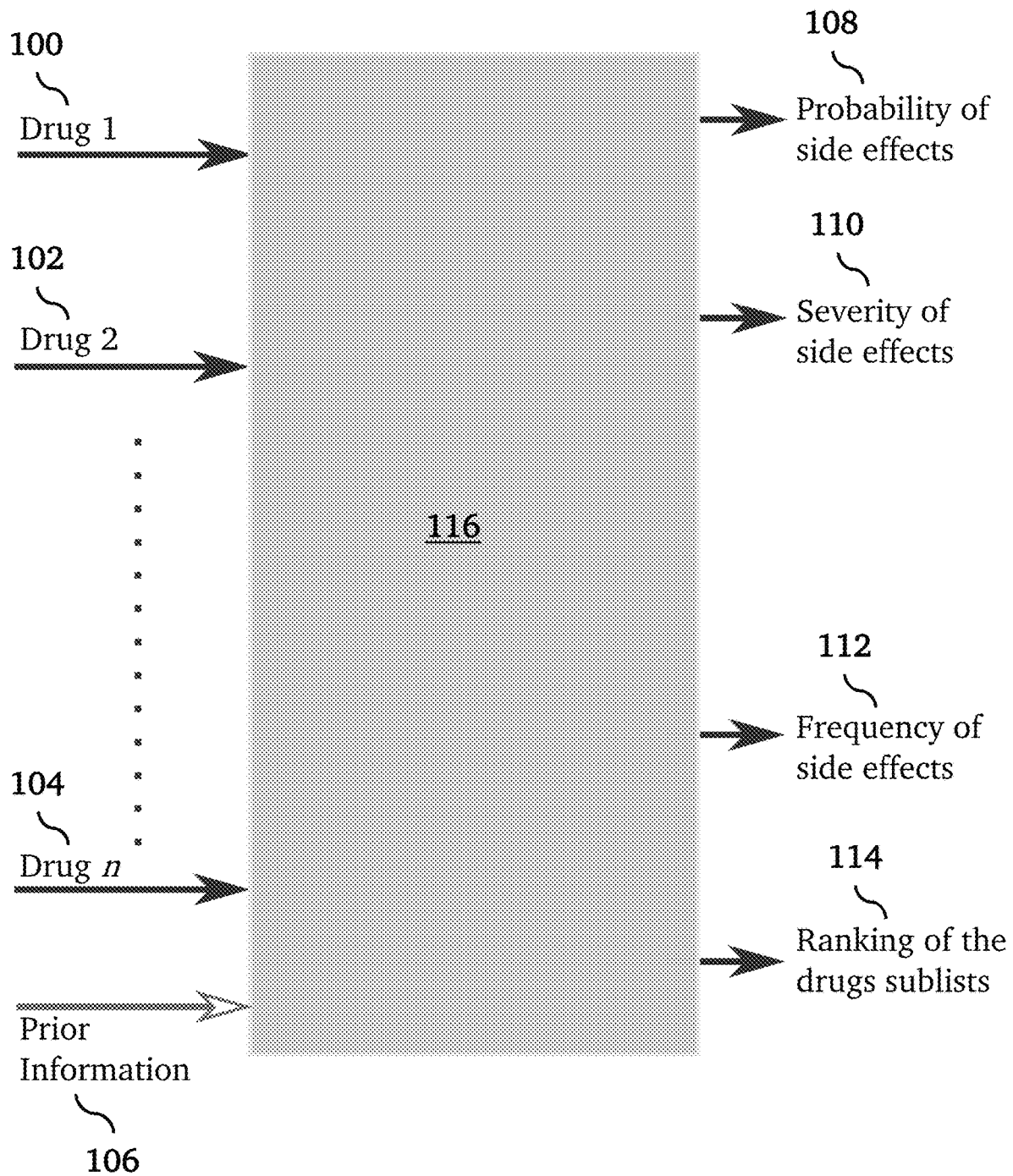
FIG. 1 is a schematic diagram providing a high-level illustration of operation of an embodiment of the present invention in a deployment stage, according to an embodiment of the invention.

The present technology uses a new type of neural network, called a multimodal cell complex neural network (MCXN), to predict for a given combination of multiple drugs the likely side effects of the combination, the severity and frequency of the side effects, and/or alternative drugs to consider. Further, the invention has the ability to predict changes in the side effects (in terms of severity and frequency) of a drug or drug combinations over a period of time (during the course of a treatment) and send notification whenever these changes occur. The MCXN has capabilities that provide both qualitative and quantitative improvements over the prior art techniques.

Our main contributions can be summarized as follows:

From a technological standpoint, we leverage a technology called multimodal cell complex networks (MCXNs). The present technology offers several advantages making it superior to existing methods (e.g., graph-based and similarity-based methods).

1. MCXNs naturally model an arbitrary number of relations making them ideal for the k-polypharmacy side-effect prediction problem. They take into consideration the higher dimensional interactions among drugs, among proteins, and between drugs and proteins, which offers better representation and leads to more accurate predictions. Existing methods (e.g., graph-based and similarity-based), on the other hand, cannot model an arbitrary number of relationships, beyond the pairwise relationship, and hence cannot be utilized to model or predict the k-polypharmacy side effects problem. The present technology (MCXN) to the k-polypharmacy side effects problem is the only existing solution for this problem (i.e., modeling arbitrary number of relationships instead of pairwise relationship).

2. MCXNs have been proven theoretically to be more expressive than all existing message passing graph neural networks making them suitable to handle the complexity that occur in complex higher order drugs-drugs interactions and provide more accurate prediction.

3. MCXNs only utilizes the local information when performing the computations, making them more efficient from practical and implementation standpoints.

4. MCXNs can efficiently model k relationships concurrently as compared to GNNs who can only model pairwise relationships. Namely, a graph model can be only model side effects between two drugs and hence these models cannot model multiple drugs, more than two, that interacts when taken concurrently.

From an application standpoint, MCXN provides an efficient solution for drugs' side effects prediction. It concurrently predicts the severity and frequency of the side effects. MCXN can also monitor and assess changes of side effects during the course of treatment (over time).

1. It is well-known that drugs' side effects vary in their severity and frequency of occurrence (two dimensions). Hence, understanding the status of a given drug (monotherapy) or drug combinations (polytherapy) on both these dimensions is critical. All existing solutions for side effects prediction were developed for either severity prediction or frequency prediction. We propose to use MCXNs for concurrently predicting both the severity and frequency for a specific drug (monotherapy) or drug combinations (polytherapy).

2. Based on the predicted severity and frequency, the present technology offers a method to rank, using dictionary order, a specific drug or drug combinations from best to worst as well as provide alternative combinations of drugs. For example, if a combination of two drugs for two different diseases causes severe and frequent side effects (worst), the present technology can recommend a better combination (mild and infrequent side effects) by replacing one or both drugs with other drugs from the same family. Automatically ranking drug combinations (based on severity and frequency) and recommending other alternatives can significantly save doctors' time and help them developing the best treatments for each patient (personalised medicine).

3. Several patients and health professionals reported incidents of changes in the drugs' side effects during the course of treatment. Specifically, it has been reported that a tolerance or an intolerance to a specific drug or drug combinations can develop over time, and new side effects can crop up well into a course of treatment. These changes in the drugs' side effects can occur due to several factors including the addition of a new drug (to treat a new health condition), changes in lifestyle, or age. To monitor changes in side effects patterns, doctors ask patients to record changes in a daily diary or log. To provide an efficient solution for this problem, we treat side effect prediction as a dynamic problem and use the present technology (MCXNs) to automatically monitor and detect changes in side effects occurring as a result of several factors (e.g., new drug, new health's condition, etc). These factors can be integrated as patient's information and used to update the model. Automatically monitoring and detecting the changes in side effects and notifying health professionals about them allows prompt detection of new patterns and adjustment of treatment plans accordingly. It also allows customization of treatment plans for each patient based on the altered side effects, which occur due to changes in the patient's lifestyle or health condition. Our model solution here is the first machine-learning based solution that handles the temporal aspect of polypharmacy side effects during the course of treatment.

4. MCXNs allows easy integration of a new drug or drug combinations and estimation of the side effects (in terms of severity and frequency) without additional training of the model. This allows pharmaceutical companies to examine potential side effects of new drugs before they reach human clinical trials or approved for actual use, which can accelerate the development of new drugs, save money, and help creating safer medicines.

FIG. 1 is a schematic diagram providing a high-level illustration of the present technology, as it operates in a deployment stage, according to an embodiment of the invention. The input during the deployment phase is a list of two or more drugs 100, 102, 104, which can be entered into a processor 116 by a physician or pharmacist prescribing the drugs to the human patient. In addition, prior information 106 of the patient (e.g. age, smoking status, patient's medical history, patient's allergy, etc) may be entered. More precisely, the input for the technology is a sequence of k drugs, k≥2 that a pharmacist wants to study or a physician wants to give to a human patient as well as the prior information of the patient. The output of the processor can be any combinations of the followings: a list of probabilities 108 with all potential side effects that the patient might have while taking these drugs, the severity category 110 of these side effects, the frequency category 112 of the side effects, and/or suggested ranked sublists 114 of the input drugs ranked by the probability, the frequency, or the severity of the side effects to help deciding on an alternative set of drugs to administer or prescribe. The processor 116 includes a multimodal cell complex neural network (MCXN) that has been appropriately trained, as will be described in detail below.

Problem Modeling

We realize the problem of side effect prediction of multiple drugs taken concurrently as a face prediction problem on a multimodal cell complex network encoding drugs, proteins, side effects relations, protein physical bindings as well as drug-protein interactions. (Multimodality is specified here with respect to cell in the given cell complex as well as the relationships. See the section on multimodal cell complexes for a more precise treatment.) More precisely, let $\mathcal{V}$ be a set of nodes that represents the set of proteins and drugs of interest. Let $\mathcal{R}$ a set of relations among the nodes representing pharmacological information among the drugs and proteins. The set $\mathcal{R}$ consists of three general categories of relations. The first category of relations describes the protein physical bindings. These relations are higher order relationships and they are identified via a tuple of the form $(v_{i_1}, \ldots, v_{i_j}, r_{i_1, \ldots, i_k})$ where $v_{i_j}$ are protein nodes and $r_{i_1, \ldots, i_k}$ is the physical binding on the tuple $(v_{i_1}, \ldots, v_{i_j})$. The second category of relations is a pairwise relationship of the form $(v_i, v_j, r_{ij})$ and describes an interaction between a drug and a protein. The third category of relations, which is the most important, is not necessarily pairwise, but is of the general form $(v_{i_1}, \ldots, v_{i_k}, r_{i_1, \ldots, i_k})$, for k≥2, where $v_{i_j}$ are drug nodes that are concurrently used. The relation r in the third category encodes the type of the polypharmacy side effect as well as the severity and the frequency of this particular side effect. These are categorical classes (f, s) associated with every r in the third category. Important to the modeling problem, the $i_k$-tuple $(v_{i_1}, \ldots, v_{i_k})$ can be thought of as a cell of a cell complex built on the top of the node set $\mathcal{V}$. This cell is spanned by the nodes $v_{i_1}, \ldots, v_{i_k}$. Given a set of k drugs $v_{i_1}, \ldots, v_{i_k}$, k≥2, our present algorithm computes the $Pr(r_{i_1, \ldots, i_k} = r)$ for r in $\mathcal{R}$. This effectively corresponds to computing the probability of having a side-effect of type r when the drugs $v_{i_1}, \ldots, v_{i_k}$ are taken concurrently by a human patient.

Figure 2:
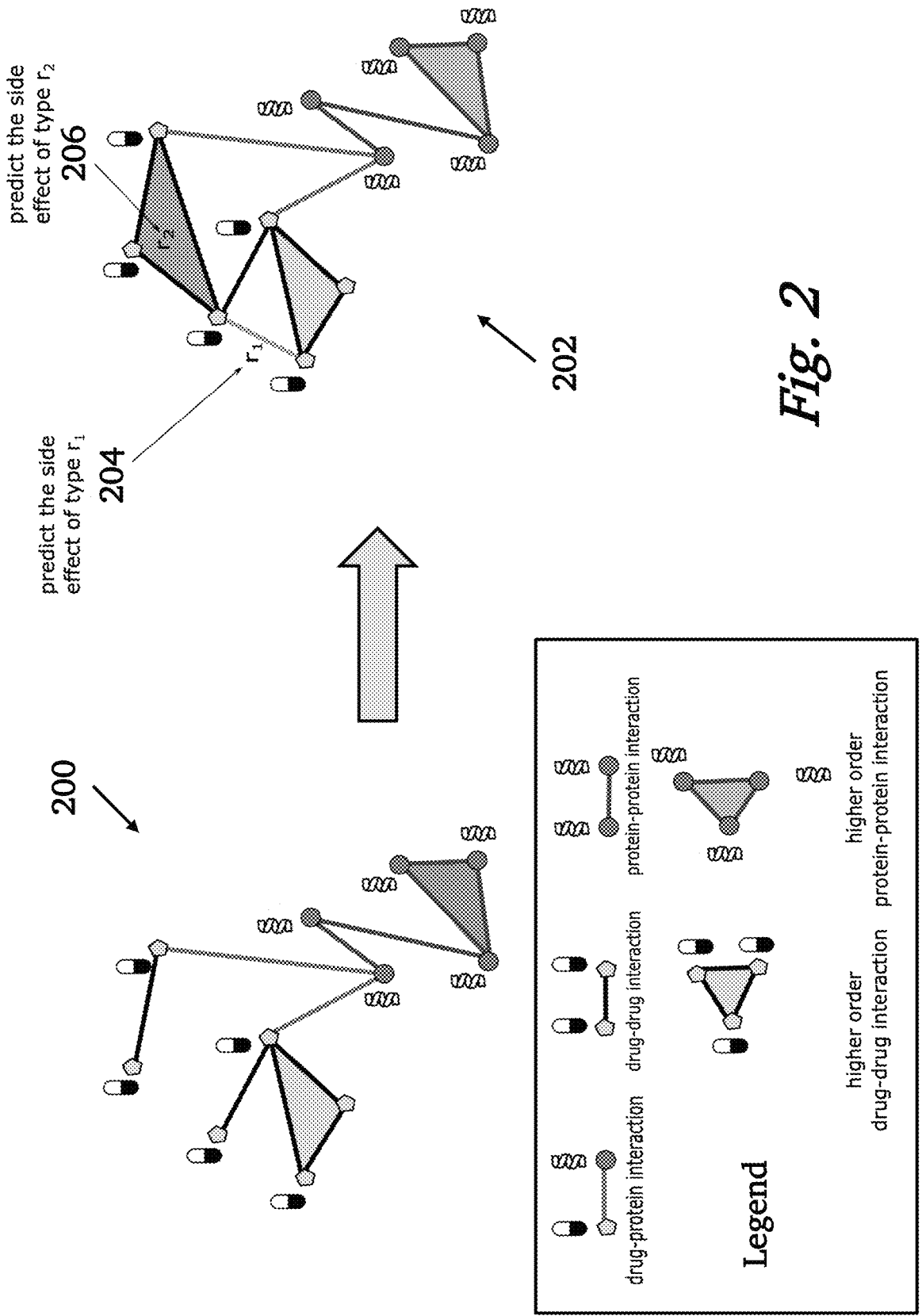
FIG. 2 is a schematic diagram providing an illustrative example of how a cell complex is used to model higher-order drug and protein interactions, according to an embodiment of the invention.

FIG. 2 is a schematic diagram providing an illustrative example of how a cell complex is used to model drug and protein relationships. On the left is shown a cell complex 200 whose nodes represent drugs and proteins and whose faces represent different types of interactions between these nodes. In particular, we have three types of interactions: drug-drug interactions, drug-protein interactions and protein-protein interactions. A face that bounds n drugs/proteins represents an interaction between these entities. (In the present description the term face is used generally to mean a k-dimensional object connecting k nodes, for any k≥2. Thus, a face can be a common edge connecting two nodes, a common surface connecting three nodes, or a common volume connecting four nodes.) The faces shown in cell complex 200 are known, i.e., represent known interactions. On the right, we show cell complex 202 representing a prediction of interactions among the set of drugs, where additional faces 204 and 206 indicate predicted interactions. As illustrated in FIG. 1, the present technology takes as input a collection of k drugs and provides the prediction that these drugs have a side-effect of type r when taken concurrently.

From the present model point of view, a side-effect between k drugs can be thought of as a face that bounds the nodes representing these drugs.

Outline of the Main Technology

Figure 4:
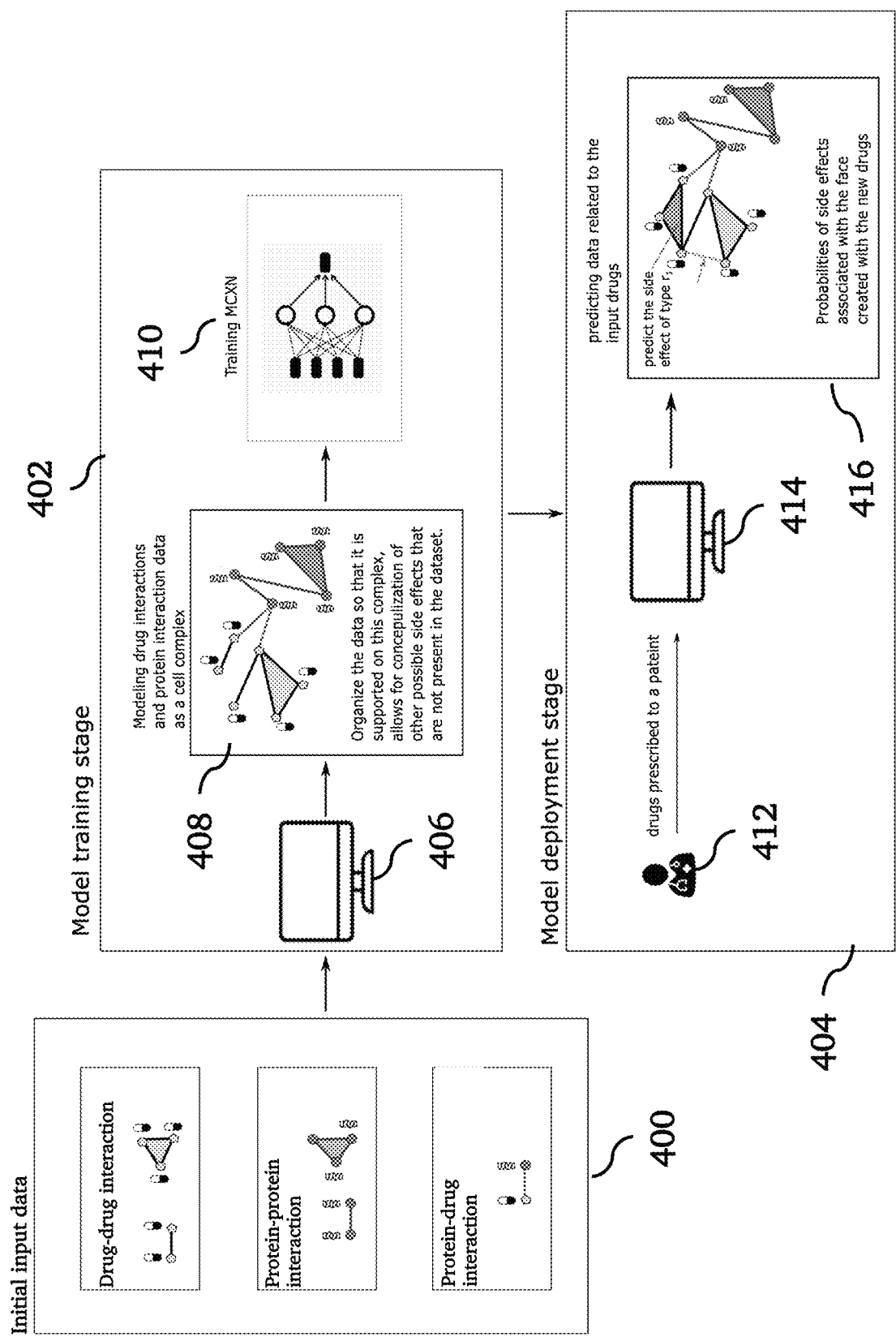
FIG. 4 is a schematic diagram illustrating an overview of a processing pipeline for the training stage and deployment stage of the present technology, according to an embodiment of the invention.

FIG. 4 is a schematic diagram illustrating a processing pipeline for the training stage 402 and deployment stage 404 of this technology. In the model training stage 402, initial input data 400 is input to a processor 406 which uses the data to model drug interactions as a cell complex 408. The initial input data 400 includes drug-drug interaction data, protein-protein interaction data, and protein-drug interaction data. The model 408 organizes this data so that it takes the form of a cell complex. This cell complex is then used to train the MCXN 410 to allow it to predict other possible side effects that are not present in the data 400. In the model deployment stage 404 the trained MCXN 410 stored in a processor 414 is used to predict from a list of drugs 412 selected for a patient interaction side effects 416 of the combination of those drugs, including probabilities of side effects associated with various combinations of the drugs not present or known in the initial data 400.

The input of the technology or the model in the training phase is the tuple $(\mathcal{V}, R)$, where $\mathcal{V}$ is a set of drugs and proteins and $\mathcal{R}$ is a set of known relations among the elements of $\mathcal{V}$, an integer $k \geq 2$ representing the maximal number of higher order drug-drug interactions that we wan to compute. The output of the model is a sequence of $$\binom{k}{j} - k$$

tensors $\mathcal{F}_r^{i_1, \ldots, i_j}$ for $2 \leq j \leq k$. The tensor $\mathcal{F}_r^{i_1, \ldots, i_j} \in (\mathbb{R}^d)^{\times j} \times \mathbb{R}^{N_r}$ is the probability that the drugs $(v_{i_1}, \ldots, v_{i_j})$ will have a side-effect of type r and d is the embedding dimension of the node set $\mathcal{V}$ and $N_r$ is the number of multi-polypharmacy side effects. Below we give the outline of the algorithm which we describe in details in the following sections.

1. Building the clique complex on the protein subgraph: For all protein nodes in V and all edges among such nodes, namely the protein-protein relations, we compute the clique complex of dimension k, which will be denoted by $\mathcal{N}_k(\mathcal{V})$. This is described in the section on building the clique complex on the protein subgraph.

2. Building the cell complex on the drug subgraph: For every higher order multi-drug relation of the form $(v_{i_1}, \ldots, v_{i_j}, r) \in \mathcal{R}$, we build a cell complex $X[(v_{i_1}, \ldots, v_{i_j}, r)]$ describing the side effects among the nodes $v_{i_1}, \ldots, v_{i_j}$. After doing this procedure for all relations in $\mathcal{R}$, we obtain a cell complex built on the top of the drug node subset of $\mathcal{V}$ encoding higher order interactions among the drug nodes in $\mathcal{V}$.

We denote the final complex obtained from step (1) and (2) by $\mathcal{X}_k$. See the section on building the cell complex on the drug subgraph for more details. The final output of these two steps is the set $\mathcal{X}_k$ and the modified relation set $\mathcal{R}'$. We call the tuple $(\mathcal{X}_k, \mathcal{R}')$ multimodal cell complex.

3. Computing node embeddings via MCXNs: We apply the multimodal cell complex network (MCXN) on $(\mathcal{X}_k, \mathcal{R}')$ to obtain node embeddings $MCXN(v) \in \mathbb{R}^d$ for every drug node $v \in \mathcal{V}$. See the section on multimodal cell complex neural network implementation.

4. Computing side-effect probabilities and severity via a MCXN-decoder: For $2 \leq j \leq k$ we compute the probability tensors $\mathcal{F}_r^{i_1, \ldots, i_j}$ using a novel multimodal cell complex decoder. See the section describing the multimodal cell complex autoencoder for more details.

The above four steps are the main steps in our present technology. Specifically steps (1) and (2) can be considered as prepossessing while steps (3) and (4) apply the present model to the processed data to obtain the multi-drug interaction predictions.

Pre-Processing the Data to a Multimodal Cell Complex

In this section we describe the algorithmic steps of preprocessing the data $(\mathcal{V}, \mathcal{R})$ to a multimodal cell complex.

Building the Clique Complex on the Protein Subgraph

In the first step of the algorithm, we build the clique complex of dimension k denoted by $\mathcal{N}_k(\mathcal{V})$ obtained from all protein nodes $\mathcal{V}_{proteins}$ and all protein relation of the form $(v_{i_1}, \ldots, v_{i_j}, r) \in \mathcal{R}$ where $v_{i_1}, \ldots, v_{i_j}$ are proteins nodes and r is a protein interaction associated with the tuple $(v_{i_1}, \ldots, v_{i_j})$. For each such as tuple we consider the clique complex $X[(v_{i_1}, \ldots, v_{i_j}, r)]$ spanned by the nodes $(v_{i_1}, \ldots, v_{i_j})$. For each such as tuple we consider the clique complex $X[(v_{i_1}, \ldots, v_{i_j}, r)]$ spanned by the nodes $(v_{i_1}, \ldots, v_{i_j})$. If a subcell in $X[(v_{i_1}, \ldots, v_{i_j}, r)]$ corresponds to a relation r in $\mathcal{R}$ then we tag this subcell by that relation.

Some subsets $S \subset \{v_{i_1}, \ldots, v_{i_j}\}$ might not have a protein interaction recorded in $\mathcal{R}$. For those subsets we associated a special auxiliary relation r' which indicates that there is no known protein interaction associated by a concurrent usage of the drugs in the set S. For all the other subcells in $X[(v_{i_1}, \ldots, v_{i_j}, r)]$ we tag them with the corresponding relation originally stored in $\mathcal{R}$.

Clique complexes can be computed using standard packages such as GUDHI (The gudhi library: Simplicial complexes and persistent homology, International congress on mathematical software, 2014, pp. 167-174).

Building the Cell Complex on the Drug Subgraph

In this step we consider all higher order multi-drug relations of the form $(v_{i_1}, \ldots, v_{i_j}, r) \in \mathcal{R}$ where $v_{i_1}, \ldots, v_{i_j}$ are drug nodes and r is a side-effect associated with the tuple $(v_{i_1}, \ldots, v_{i_j})$.

The procedure of building a complex from these relations is similar to the procedure we provided above in the section on building the clique complex on the protein subgraph. However, for concreteness we repeat these steps here.

For each relation $(v_{i_1}, \ldots, v_{i_j}, r)$ where $v_{i_j}$ is a drug we consider the clique complex $X[(v_{i_1}, \ldots, v_{i_j}, r)]$ spanned by the nodes $(v_{i_1}, \ldots, v_{i_j})$. If a subcell in $X[(v_{i_1}, \ldots, v_{i_j}, r)]$ corresponds to a relation r in $\mathcal{R}$ then we tag this subcell by that relation.

Some subsets (or subcells) $S \subset \{v_{i_1}, \ldots, v_{i_j}\}$ might not have a side-effect recorded in $\mathcal{R}$. For those subsets we associated a special auxiliary relation r" which indicates that there is no known side-effect associated by a concurrent usage of the drugs in the set S. For all the other subcells in $X[(v_{i_1}, \ldots, v_{i_j}, r)]$ we tag them with the corresponding relation originally stored in $\mathcal{R}$.

We denote the final complex obtained from the section describing building the clique complex on the protein subgraph and the section describing building the cell complex on the drug subgraph by $\mathcal{X}_k$. The final output of these two steps is the set $\mathcal{X}_k$ and the modified relation set $\mathcal{R}'$. As we mentioned earlier, the tuple $(\mathcal{X}_k, \mathcal{R}')$ is called the multimodal cell complex. This tuple will be the input to multimodal cell complex network, whose implementation we describe next.

Multimodal Cell Complex Neural Network Implementation

In this section we introduce the detailed implementation and mathematical background for a multimodal cell complex network (MCXN). The implementation of MCXN is explained in the section on multimodal cell complex networks.

Cell Complexes

A cell complex is a construct that is built from primitive objects called cells. The 0-cells in a cell complex represent the most primitive entities. For our purpose these entities are the drugs and the proteins. Among the 0-cells we define higher dimensional relations, or k-cells.

For our purpose, these k-cells represent higher order relationship between the 0-cells. In other words, they represent a side effect if these 0-cells correspond to drugs and protein interaction if they are proteins. In particular, 1-cells represent pairwise interactions: drugs-drugs proteins-proteins and proteins-drugs which as we described earlier are inadequate to higher order complex interactions that naturally occur. In our application higher order interactions can be multi-proteins interactions, multi-proteins and multi-drugs interactions and multi-drugs interactions. Mathematically, cell complexes are represented via adjacency sparse matrices. An example is given in FIG. 3. Computationally, these matrices are sparse which allows for a fast and practical implementation.

Figure 3:
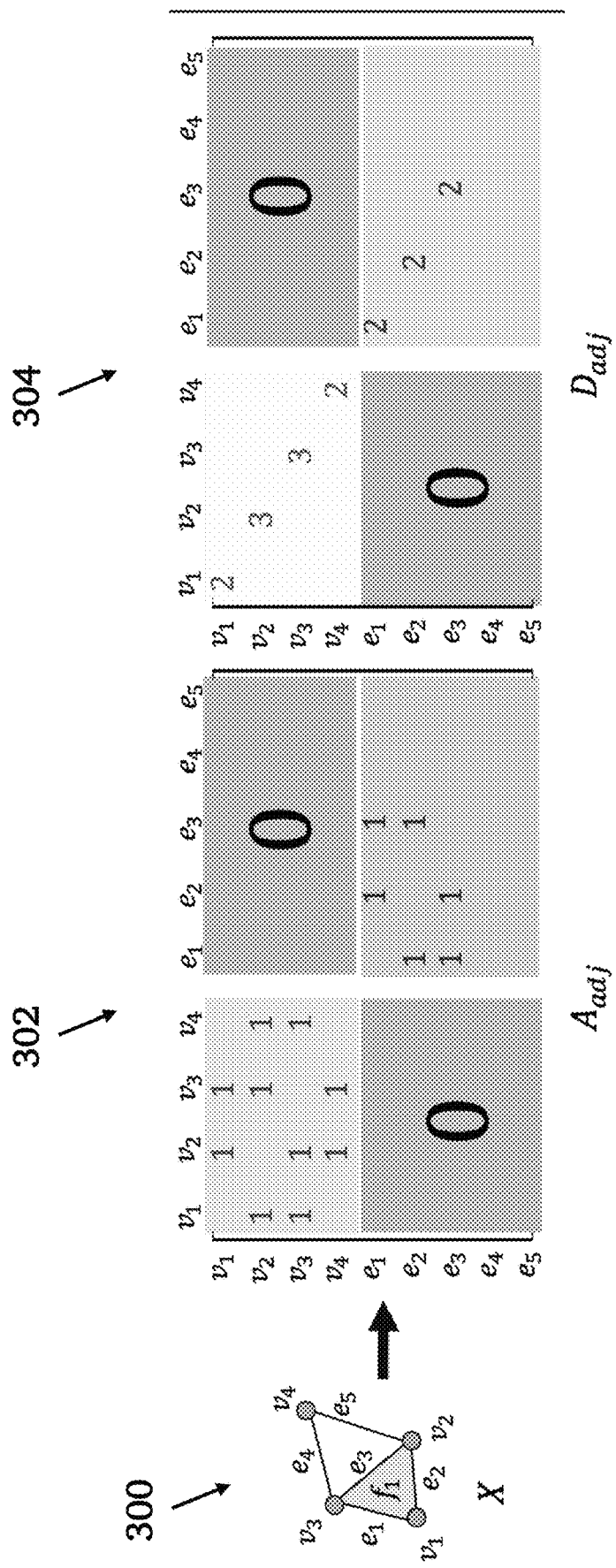
FIG. 3 is a schematic diagram illustrating examples of adjacency matrices for a cell (or a simplicial) complex, according to an embodiment of the invention.

FIG. 3 is a schematic diagram illustrating examples of adjacency matrices for a cell (or a simplicial) complex 300. The matrix 302 is the adjacency matrix $A_{adj}$ of the simplicial complex X 300. The matrix 304 is the adjacency degree matrix $D_{adj}$ of the simplicial complex X 300. The non-zero upper left and lower right submatrices in $A_{adj}$ represent $A_{adj}^0$ and $A_{adj}^1$ of a cell complex X, respectively.

To explain the algorithm we need some notations. For a cell $c^m$ of dimension m in a cell complex $\mathcal{X}$, we will denote its adjacent cells of dimension m by $\mathcal{N}(c^m)$. We will denote to the cells in $\mathcal{X}$ that are larger than a certain dimension k by $\mathcal{X}^{>k}$. We define $\mathcal{X}^{<k}$ similarly.

Two cells in $\mathcal{X}$ are said to be adjacent if they are both a boundary of higher dimensional cell in X. Furthermore, we will denote by $\mathcal{N}_r(c^m)$ to the cells adjacent to m via higher dimensional cell that carries the relation r.

Multimodal Cell Complexes

A multimodal cell complexes is a cell complex $\mathcal{N}_r$ with a mapping $\mathcal{R}: \mathcal{X}^{>0} \to \mathcal{C}$ that associates to every cell $x \in \mathcal{X}$ a "color" $\mathcal{R}(x)$ in $\mathcal{C}$. The set $\mathcal{C}$ is a finite set and we think of it as the set of all "colors" that colors the cells in $\mathcal{X}^{>0}$. The data above is hence specified by the tuple ($\mathcal{X}$, $\mathcal{R}$). In our case multimodality is not only defined with respect to higher dimensional cells but also with respect to the zero cells. However, we treat multimodality of the zero cells differently since they corresponds to proteins and drugs whereas the multimodality on the faces of $\mathcal{X}$ corresponds to relations among the proteins and drugs.

Multimodal Cell Complex Networks

We now describe the multimodal cell complex network. This model takes the multimodal cell complex ($\mathcal{X}_k$, $\mathcal{R}'$) we obtained from steps described in the section on building the clique complex on the protein subgraph and the section on building the cell complex on the drug subgraph, and produces an embedding $z_i$ for every node $v_i \in \mathcal{V}$ representing a drug.

Computationally, the forward propagation of a multimodal cell complex neural net requires the following data as inputs: (1) A cell complex $\mathcal{X}$ of dimension n and (2) For each m-cell $c^m$ in $\mathcal{X}$, we have an initial vector $h_{c^m}^{(0)} \in \mathbb{R}^{l_m^0}$. These initial vectors $h_{c^m}^{(0)} \in \mathbb{R}^{l_m^0}$ can be chosen to be unique one-hot vectors for every cell in the complex $\mathcal{X}$.

Precisely, given the desired depth L>0 of the net one wants to define on the complex $\mathcal{X}$, the forward propagation algorithm on $\mathcal{X}$ consists of L×n multimodal inter-cellular message passing schemes defined for $0 < k \leq L$:

$$h_{c^0}^{(k)} := \phi\left(\sum_r \sum_{a^0 \in N_r(c^0)} W_{a^0}^{(k-1),r} h_{a^0}^{(k-1)} + h_{c^0}^{(k-1)}\right) \in \mathbb{R}^{l_0^k}, \quad (1)$$

$$h_{c^{n-1}}^{(k)} := \phi\left(\sum_r \sum_{a^{n-1} \in N_r(c^{n-1})} W_{a^{n-1}}^{(k-1),r} h_{a^{n-1}}^{(k-1)} + h_{c^0}^{(k-1)}\right) \in \mathbb{R}^{l_{n-1}^k} \quad (2)$$

where $h_{a^m}^{(k)}$, $h_{c^m}^{(k)} \in \mathbb{R}^{l_m^k}$ are the hidden states of cells $a^m$, $c^m$ respectively in the k-th layer of the cell complex network. Moreover, $W_{a^m}^{(k),r}$ is a relation-specific and dimension-specific trainable weight matrix. Finally the function $\phi$ is a non-linear function. This can be chosen to be a standard non-linear function such as RELU. In our application we suggest the depth of the model L to be 3. Furthermore, in the output layer we only care about the output of the 0-cells, $h_{c^0}^{(L)}$, which represent the embeddings of the protein and the drug cells.

Note that implementation of the equations that describe multimodal cell complex network above can be done using standard graph neural networks such as Geometric Pytorch (Fey et al., Fast graph representation learning with pytorch geometric, arXiv preprint arXiv:1903.02428 (2019)). The only input that is really required is the adjacency matrices of the cell complex $\mathcal{X}_k$, which we computed in the section on building the clique complex on the protein subgraph and the section on building the cell complex on the drug subgraph, as well as the relations $\mathcal{R}$ which are given with the input dataset.

Multimodal Cell Complex Autoencoder and Computing the Probability Tensors of Multi-Drugs Side Effects The output that we obtain in the last step in the section on cell complexes is the node embeddings $z_i$ obtained by evaluating the multimodal cell complex network on every drug node in $\mathcal{V}$.

In this final step of our present algorithm we want to compute the final probability tensors of higher order drug-drug interactions. To this end, assume we are given j embeddings $z_{i_1}, \ldots, z_{i_j}$ representing j drugs $v_{i_1}, \ldots, v_{i_j}$ and we want to compute the probability of a side-effect r when these drugs are taken concurrently. We define the multimodal cell complex decoder associated with the side-effect r:

$$\text{dec}_r^j : (\mathbb{R}^d)^{\times j} \to \mathbb{R} \quad (3)$$

where $$(z_{i_1}, \ldots, z_{i_j}) \to M_r^{i_1, \ldots, i_j}(z_{i_1})_{l_1} \cdots (z_{i_j})_{l_j} \quad (4)$$

where $M_r \in (\mathbb{R}^d)^{\times j}$ is a trainable diagonal tensor associated with the side-effect r. Finally the probably tensor $\mathcal{P}_r^{i_1, \ldots, i_j}$ is given by $$\mathcal{P}_r^{i_1, \ldots, i_j} = \sigma(\text{dec}_r^j(z_{i_1}, \ldots, z_{i_j})) \quad (5)$$

where $\sigma$ is the usual sigmoid function $$\sigma(x) = \frac{1}{1 + \exp(-x)}.$$

Integrating Prior Information about the Patient

The priori of the patient is a vector $v \in \mathbb{R}^k$ describing different factors that might lead to a change in the side effects. This feature vector is described by concatenation of factors that might lead to a change in the side effects. Examples of these factors include the addition of a new drug, adjustments of old drugs (e.g., increase or decrease doses), changes in the patient's health condition (e.g., new allergy), or changes in the lifestyle (e.g., smoking habits), among other factors. All categorical features of the patient are converted to numerical are converted to numerical features using known classification techniques.

Our model can be modified to take the priori of the patient into consideration while computing the side effects probabilities as follows. We assume as before that we are given j embeddings $z_{i_1}, \ldots, z_{i_j}$ representing j drugs $v_{i_1}, \ldots, v_{i_j}$ and we want to compute the probability of a side-effect r when these drugs are taken concurrently by a human patient with a vector v. We combine the vector v with the vectors $z_{i_j}$ as follows:

$$z'_{i_j} = \text{RELU}(W[z_{i_j}, v] + b) \quad (6)$$

where W an b are trainable weight parameters and [a, b] denotes the concatenation of the vectors a and b. Finally the vectors $z'_{i_1}, \ldots, z'_{i_j}$ are used with the multimodal cell complex decoder in Eq. 4 and finally injected into Eq. 5 to obtain the final probabilities.

Training the Final Model

To train the model we generalize known methods (Mikolov et al., Distributed representations of words and phrases and their compositionality, Advances in neural information processing systems, 2013, pp. 3111-3119; and also see Zitnik et al.) to cell complexes as follows. We want our model to associate higher probabilities to observed cells $(v_{i_1}, \ldots, v_{i_j}, r)$ over random non-cells which are not associated with a particular side-effects. To this end we define the loss:

$$J_r(i_1, \ldots, i_j) = -\log(\mathcal{P}_r^{i_1, \ldots, i_j}) - \mathbb{E}_{(n_2, \ldots, n_j) \sim P_r(i_2, \ldots, i_j)} \log(1 - \mathcal{P}_r^{i_1, n_2, \ldots, n_j}) \quad (7)$$

For each j-drug tuple $(v_{i_1}, \ldots, v_{i_j}, r)$ (positive example) we sample a random tuple, a cell, $(v_{i_1}, \ldots, v_{i_j}, r)$ (negative example) by randomly selecting j–1 nodes $(n_2, \ldots, n_j)$ sampled from the distribution $P_r(i_2, \ldots, i_j)$. Putting all cells together we obtain the loss $$J_{prob} = \sum_{(v_{i_1}, \ldots, v_{i_j}, r) \in \mathcal{R}'} J_r(i_1, \ldots, i_j) \quad (8)$$

Prediction: Side-Effect Frequency and Severity Over Time

In this section we explain how our algorithm can be utilized for frequency and severity predictions of a drug side effect. To build these models we assume that we are given the same data as before ($\mathcal{V}, \mathcal{R}$). However, we also assume that every relation r∈$\mathcal{R}$ is equipped with two categories classes: side effect frequency and side effect severity. We give precise definition of these terms below. The categories of the frequency and the severity associated with the relations will help us casting the prediction of these quantities as a classification problem. We provide details next.

Side-Effect Frequency Prediction

Predicting the frequency of a drug side-effect is also a desirable feature and our model can be utilized for this purpose.

From a technical stand-point we realize the frequency problem as a classification problem where we define 6 categories for the side-effect frequency: zero, very rare, rare, infrequent, frequent, and very frequent.

To this end, we start by assuming that we are given j embeddings $z_{i_1}, \ldots, z_{i_j}$ representing j drugs $v_{i_1}, \ldots, v_{i_j}$ and our goal is to predict the frequency class. More precisely, we want to predict the class $$\overline{h}_{[v_{i_1}, \ldots, v_{i_j}]}$$

in $\mathbb{R}^6$. Here 6 is the number of the side-effect frequencies categories that we specified above. We learn a weighted sum of the embeddings $z_{i_1}, \ldots, z_{i_j}$ by learning the function $$\overline{h}_{[v_{i_1}, \ldots, v_{i_j}]} = \sum_{m=1}^{j} \overline{w}_m([v_{i_1}, \ldots, v_{i_j}]; W_r) z_{i_m} \quad (9)$$

where $\overline{w}_m([v_{i_1}, \ldots, v_{i_j}]; W_r) \in \mathbb{R}$ is a weight of the embedding $z_m$ that depends on $z_{i_1}, \ldots, z_{i_j}$ and is parametrized by $W_r \in \mathbb{R}^{6 \times d}$, a trainable weight matrix that depends on the side-effect r and given explicitly via:

$$\overline{w}_m([v_{i_1}, \ldots, v_{i_j}]; W_r) = \sigma\left((z_m)^T . RELU\left(W_r \sum_{n=1}^{j} z_{i_n}\right)\right), \quad (10)$$

where $$\sigma(x) = \frac{1}{1 + \exp(-x)}.$$

The final network is trained with the conventional multi-class cross entropy loss using ground truth labels on set $\mathcal{R}$ representing the frequency of the drug effect.

Side-Effect Severity Prediction

The severity of a certain effect can also be realized as a classification problem. One possible categorization is: very rare, rare, frequent, and very frequent. From technical standpoint the severity prediction with our model is not different from that of frequency described above. The only difference is that the classes of severity are utilized during the training of the networks instead of the frequency.

Ranking of Drug Combinations

Based on the generated severity and frequency, the probabilities and severity scores, we can rank drugs from best combination to worst combination. Given a j drugs $(v_{i_1}, \ldots, v_{i_j})$, the system provides the probabilities of potential side effects a patient may have by taking the drugs $(v_{i_1}, \ldots, v_{i_j})$ concurrently, the severity of these side effects and their frequency. It also provides the same measurements for all possible combinations of $(v_{i_1}, \ldots, v_{i_j})$. For every side-effect r and for every combination l of $(v_{i_1}, \ldots, v_{i_j})$ we essentially have three scores $\{(s_l, p_l, f_l)\}_{i=1}^{L}$ where $s_l$ is the severity, $p_l$ is the probability and $f_l$ is the frequency. Here L is the total number of all possible combinations of the drug list $(v_{i_1}, \ldots, v_{i_j})$ having probabilities larger than a certain threshold. The list $\{(s_l, p_l, f_l)\}_{i=1}^{L}$ can be ordered by dictionary order: in this case a combination with smaller severity are ranked first, when two combinations have the same severity then their probabilities are considered and finally the frequency. This order can be changed based on the judgment of the physician.

Monitoring Changes in Drugs' Side Effects

MCXN can be utilized for monitoring changes in drugs' side effects. Namely, whenever the patient starts to take a new drug, we re-calculate the probabilities, severity and frequency using our models. In other words, if there is a change to the input to the model, we recompute the outputs: probabilities, severity and frequency.

Prediction of Side Effects of a New Drug

It also sometimes desirable to know the potential side effects of a new drug when used concurrently with existing more well-studied drugs.

Technically, the model is trained on the dataset $(\mathcal{V}, \mathcal{R})$ where $\mathcal{V}$ is the set of drugs and proteins. Now, suppose that we have new drug v that does not belong to $\mathcal{V}$ and we want to check the side effects of v when taken concurrently with drugs $v_{i_1}, \ldots, v_{i_j}$. This can be done using our model by the following steps:

1. For the drug v we predict all its protein interactions. This can be done in multiple methods such as graph based methods (Yang et al., Graph-based prediction of protein-protein interactions with attributed signed graph embedding, BMC bioinformatics 21 (2020), no. 1, 1-16).
2. Now that the we have the protein-drug interaction we can run the algorithm described in section describing the multimodal cell complex autoencoder on (v, $v_{i_1}, \ldots, v_{i_j}$, r) to predict the probability of having a side-effect r when using the drugs (v, $v_{i_1}, \ldots, v_{i_j}$) concurrently.

Observe that the above two steps require no new training for the neural network. In other words, the trained neural network described in the section describing the multimodal cell complex autoencoder is sufficient to make the side-effect probabilities on the cell (v, $v_{i_1}, \ldots, v_{i_j}$).

Implementation, Training, and Deployment

Specialized Python Libraries Built to Support the Technology

To develop the technology present herein, we have completely and comprehensively built two python libraries that are tailored towards building and developing our application quickly and efficiently. Specifically, the first library is developed to build higher order networks such as cell complexes, simplicial complex, hypergraph, and cell complexes while the second library is developed to train models supported on these higher order networks.

Our two libraries support the following features
1. Building a cell complex with arbitrary dimension. In particular, our cell complex library supports the modeling of the cell complex nodes as drugs and the modeling of the side effects as higher order cells in that cell complex.
2. After building the drug/side effect complex, our libraries support building sparse and massive adjacency as well as the incidence matrices required to train the model as specified in Eq. 1 and Eq. 2.
3. Beyond modeling drugs and side effects in terms of the elements of the cell complex, our libraries support attaching any type of data to various parts of the cell complex representing the drugs and their side effects. This data can be vector data obtained during various stages of training/testing/deployment, or any other drag-related data one may wish to attach to the drug or the side effect during any stage of training/testing/deployment. Our libraries also support the manipulation of this data, whenever applicable, with other popular python libraries such as Numpy, Scipy, TensorFlow and Pytorch. This facilitates fast and practical implementation and deployment of the present technology.
4. After building the drug/side effect complex, attaching various data elements to various elements of this complex, our library supports building and training any higher order model; in particular, it supports building a model as specified in Eq. 1, Eq. 2, Eq. 9, Eq. 10, and Eq. 7.

To facilitate fast computation over massive relational data, we exploit the sparse matrices capabilities available in PyTorch Geometric (Fey et al., Fast graph representation learning with PyTorch Geometric, Iclr workshop on representation learning on graphs and manifolds, 2019). Note that we only exploit this feature from PyTorch Geometric, but the rest of the library is novel and contains new functions that allow computing the probability tensors of multi-drugs side effects.

Required Datasets

To train the present technology (MCXN), any dataset $(\mathcal{V}, \mathcal{R})$ with the following features can be used: (1) prior information about the patients, (2) a list of drugs, (3) a list of proteins, (4) a list of relations $\mathcal{R}$ among the proteins and drugs representing pharmacological information among the drugs and proteins. The lists (2) and (3) are called the node sets in our document and they are denoted by $\mathcal{V}$ which is simply a list of the form $\{v_1, \ldots, v_N\}$, where each $v_i$ represents a protein or a drug. The set $\mathcal{R}$ consists of three general categories of relations given as three lists. We describe these relations next.

1. The first category of relations describes the protein physical bindings. These relations can be a string form $(v_{i_1}, \ldots, v_{i_j}, r_{i_1}, \ldots, i_k)$, where $v_{i_j}$ are protein nodes and $r_{i_1}, \ldots, i_k$ is the physical binding on the tuple $(v_{i_1}, \ldots, v_{i_j})$.
2. The second category of relations is a pairwise relationship of the form $(v_i, v_j, r_{ij})$ to describe the interaction between a drug and a protein.
3. The third category of relations has the following form $(v_{i_1}, \ldots, v_{i_k}, r_{i_1}, \ldots, i_k)$, for k≥2, where $v_{i_j}$ represent drugs that are concurrently used. Any relation r in the third category encodes the type of the k-polypharmacy side effect as well as the severity and the frequency of this particular side effect. The severity and the frequency of a side effect is represented by a pair of the form (f, s), where f and s are categorical classes associated with every r of the third category.

MCXN Training

To train our model with out library, we first need to specify the adjacency/incidence matrices obtained from the multimodal cell complex $(\mathcal{X}_k, \mathcal{R})$ as well as the initial vectors $h_c^{(0)}$, which are chosen to be one hot encoder vectors. We refer to the section on building the clique complex on the protein subgraph and the section on building the cell complex on the drug subgraph for explanations of the prepossessing of $\mathcal{X}_k$ as well as the prepossessing of the relations $\mathcal{R}$ which are given with the input dataset. The adjacency/incidence matrices can be computed using the two libraries that we have built and described their content in the section on specialized python libraries.

After specifying the input, MCXN is then trained using standard stochastic gradient descent similar to a regular graph neural network (Chen et al., Stochastic training of graph convolutional networks with variance reduction, arXiv preprint arXiv:1710.10568 (2017)). Our two libraries natively support training these models once the drug complex is built and the data is correctly attached to various elements in this complex. Finally, the hyperparameters of the training procedure are specified using Bayesian optimization during training (Springenberg et al., Bayesian optimization with robust bayesian neural networks, Advances in neural information processing systems 29 (2016), 4134-4142).

As for the hardware specification, it is recommended to utilize the new AI accelerators such as Google's Tensor Processing Units (TPU) or Intel's Nervana Neural Network Processor. Such solutions allow for massive computing capacity and are well-suited for sparse matrix computation, which are needed for our training. We refer to Balog et al. (Fast training of sparse graph neural networks on dense hardware, arXiv preprint arXiv:1906.11786 (2019)) for a recent hardware specification of training graph neural networks on the modern AI accelerators.

MCXN Deployment in Practice.

When working with neural networks in general, we have two phases: a training phase and a deployment phase. In our case, once the MCXN is trained on the datasets ($\mathcal{V}$, $\mathcal{R}$) it can be utilized to infer results on new drugs and infer the side effects between a set of drugs as explained above. To infer the results on a set of k drugs, the user input these drugs to the program and then these drugs are mapped to their one hot encoder representation which are then fed into the network to compute the probabilities, frequency and severity of the side effects.

It is worth emphasizing that although cell complex nets rely on higher order interactions to provide the prediction, they only require sparse matrices to store the data of the complexes; sparse matrices are fast and reliable in practical applications. All our computations supported in our libraries support these computations and we have built our technology with this scalable performance in mind.

Preliminary Results

We provide here an initial evaluation of our technology on drug side effects prediction. Note that the dataset in Zitnik et al. contains triplet side effects (k=3). Moreover, the technique described in Young et al. (Young et al., Hypergraph reconstruction from network data, Communications Physics 4 (2021), no. 1, 1-11) allows the conversion of any graph side-effect data to multi-way relational data as we use to train our model. The architecture that is used for prediction is demonstrated above in the description of multimodal cell complex networks. We built this architecture using our first library, and trained this architecture (as described above) using our second library. The present technology achieved predictive accuracy of approx. 91%. It is worth mentioning that as far as we know our method is the only method that can handle multi-drug side effect prediction; all current methods, including graph-based methods, can only handle binary side effect prediction. It is also worth mentioning that our method requires a significantly lower number of epochs to train (40 epochs) making it easy to deploy and update in practice.

The invention claimed is:

1. A method for predicting side effects of a combination of drugs administered concurrently, the method comprising:
    (a) training a multi-modal cell complex neural network (MCXN) on a dataset, wherein the MCXN includes nodes representing the drugs and proteins, pair-wise relationships between nodes representing interactions between pairs of drugs and/or proteins, and k-wise relationships between the nodes representing interactions between k drugs and/or proteins, where k>2; wherein the dataset includes a list of drugs, a list of proteins, and pharmacological information about the drugs in the list of drugs and proteins in the list of proteins; wherein the pharmacological information about the drugs and the proteins include: i) physical binding information of the proteins, ii) interactions between the drugs and the proteins, iii) interactions between two or more of the drugs, including severity and frequency of side effects of the interactions;
    (b) inputting to the MCXN a specification of the combination of drugs to be administered concurrently, where the combination includes at least three drugs, wherein the at least three drugs includes a drug not included in the training set;
    (c) predicting from the MCXN probabilities that administering the combination of drugs concurrently results in potential side effects, and predicting both frequencies of the potential side effects and severities of the potential side effects.

2. The method of claim 1 further comprising outputting a list of the probabilities of the potential side effects resulting from administering the combination of drugs concurrently.

3. The method of claim 1 further comprising outputting a severity category of the potential side effects resulting from administering the combination of drugs concurrently.

4. The method of claim 1 further comprising outputting a frequency category of the potential side effects resulting from administering the combination of drugs concurrently.

5. The method of claim 1 further comprising outputting ranked sublists of the input drugs ranked based on a combination of frequency and the severity of side effects.

6. The method of claim 1 further comprising inputting to the MCXN prior patient health information over a time period and outputting resulting changes in frequency and severity of side effects over the time period.

7. The method of claim 6 wherein prior patient health information over a time period includes changes in an administered drug, changes in a drug dose, changes in a health condition, or changes in lifestyle.

* * * * *